United States Patent [19]

Gibson et al.

[11] Patent Number: 4,570,019

[45] Date of Patent: Feb. 11, 1986

[54] METHOD OF PREPARING POLYETHYLENE POLYAMINES HAVING IMPROVED COLOR

[75] Inventors: Charles A. Gibson, South Charleston; John W. Crandall, Charleston, both of W. Va.

[73] Assignee: Union Carbide Corporation, Danbury, Conn.

[21] Appl. No.: 577,323

[22] Filed: Feb. 8, 1984

Related U.S. Application Data

[63] Continuation of Ser. No. 398,864, Jul. 16, 1982, abandoned, which is a continuation of Ser. No. 238,128, Feb. 25, 1981, abandoned.

[51] Int. Cl.⁴ .................. C07C 85/00; C07C 85/26
[52] U.S. Cl. .................................. 564/498; 564/497; 564/511; 564/512
[58] Field of Search ............... 564/498, 497, 511, 512

[56] References Cited

U.S. PATENT DOCUMENTS

| | | | |
|---|---|---|---|
| 3,168,569 | 2/1965 | Matell | 564/497 X |
| 3,207,790 | 9/1965 | Glew et al. | 564/497 |
| 3,217,026 | 11/1965 | Vertnik et al. | 564/498 X |
| 3,595,921 | 7/1971 | Pitts | 564/498 |
| 3,723,529 | 3/1973 | Pitts et al. | 564/498 |
| 3,819,710 | 6/1974 | Jordan | 564/497 |

FOREIGN PATENT DOCUMENTS

| | | | |
|---|---|---|---|
| 1071711 | 12/1959 | Fed. Rep. of Germany | 564/498 |
| 2163516 | 7/1972 | Fed. Rep. of Germany | 564/498 |
| 1351050 | 4/1974 | United Kingdom | 564/498 |

*Primary Examiner*—Paul F. Shaver
*Attorney, Agent, or Firm*—Norman L. Balmer

[57] ABSTRACT

A process is provided which may be run continuously for producing polyethylene polyamines having improved color characteristics which comprises treating discolored polyethylene polyamines with polyethylene polyamine hydrochloride in the presence of water at elevated temperatures for the time necessary to reduce the color of said polyethylene polyamines and then flash evaporating the decolorized polyethylene polyamines from the treating mixture.

19 Claims, No Drawings

METHOD OF PREPARING POLYETHYLENE POLYAMINES HAVING IMPROVED COLOR

This application is a continuation of application Ser. No. 398,864, filed 7/16/82 now abandoned, which is in turn a continuation of Ser. No. 238,128, filed 2/25/81, now abandoned.

BACKGROUND OF THE INVENTION

The present invention relates to a process for decolorizing polyethylene polyamines and, more particularly, to a process for producing polyethylene polyamines having improved color characteristics by treatment with hydrochloric acid which may be run continuously.

It is well known that polyethylene polyamines, and particularly the higher polyamines, become discolored during their preparation which generally reduces their commercial value. Heretofore, various procedures have been used commercially or suggested for decolorizing or otherwise improving the color of these compounds including, for example, treating with hydrogen chloride or amine hydrochlorides as disclosed in U.K. Pat. No. 1,351,050; treatment with activated carbon at elevated temperatures (about 200° C.); treatment with potassium hydroxide; and treatment with zinc metal, zinc metal and water, or zinc metal and an alkali. In each of these procedures, distillation is generally a final step needed to achieve the desired color, and neutralization of residues, handling and separation of metal powders, or reactivation of the treatment medium require special apparatus which complicate the process. Moreover, to the best of our knowledge none of these procedures are completely suitable for the continuous preparation of decolorized polyamines.

It would, thus, be highly desirable if a process was developed which was generally simple but could be employed to decolorize various polyamines, and particularly the higher polyamines, to obtain color levels of 100 Platinum-Cobalt or less, that did not require special or complicated apparatus and/or procedures, and did not involve the handling or disposal of treating materials. A process that could be used to continuously prepare decolorized polyamines would be particularly advantageous.

SUMMARY OF THE INVENTION

In accordance with the present invention there is provided a process for producing polyethylene polyamines having a low color of the general formula:

$NH_2(CH_2CH_2NH)_nH$ where n is an integer of 1 to 5 from discolored polyethylene polyamines which comprises treating discolored polyethylene polyamines with polyethylene polyamine hydrochloride in the presence of water at elevated temperatures for the time necessary to reduce the color of said polyethylene polyamines and then flash evaporating the decolorized polyethylene polyamines from the treating mixture. Preferably the decolorization step (digestion step) is carried out under pressures high enough to maintain water in the liquid phase.

The decolorized polyethylene polyamines that are separated from the treatment mixture during the flash evaporation step of the process contain up to 80-85 percent of the discolored polyamines that were treated along with substantially all the water from the mixture, but the decolorized polyamine product can be readily separated from the water by means well known in the art without the need for neutralization or similar procedures. It has also been discovered that the residue mixture in the evaporator contains polyamine hydrochlorides which may be used for decolorizing of discolored, crude polyethylene polyamines when a small amount of water is added to the treatment mixture prior to carrying out the decolorization step. Thus, the need for discarding the polyamine hydrochloride-containing residue composition or even the need for any neutralization step is eliminated.

In accordance with the present invention there is also provided a continuous process for producing polyethylene polyamines having improved color properties as hereinabove described which comprises treating a discolored polyethylene polyamine with polyethylene polyamine hydrochloride in the presence of water at elevated temperatures for the time necessary to prepare decolorized polyethylene polyamines, flash evaporating the decolorized polyethylene polyamine from said treatment mixture as hereinabove disclosed and then employing the polyamine hydrochloride residue from said flash evaporation step in treating further amounts of discolored polyethylene polyamines in the presence of water at elevated temperatures.

The process of the invention may be used to readily treat discolored, crude polyethylene polyamines with colors up to a Gardner Scale No. 14 or even higher to obtain polyethylene polyamines with a low color of 100 Platinum-Cobalt or even less.

DESCRIPTION OF THE INVENTION

According to the present invention there is provided a process for producing decolorized polyethylene polyamines of the general formula:

$NH_2(CH_2CH_2NH)_nH$ wherein n is an integer of 1 to 5 from discolored polyethylene polyamines of the same general formula which comprises treating said discolored polyethylene polyamines with polyethylene polyamine hydrochloride in the presence of water at pressures and temperatures to be more fully described hereinafter for the time necessary to reduce the color of said discolored polyethylene polyamine. The decolorized polyethylene polyamine treatment solution is then subjected to flash evaporation conditions which readily separates substantial amounts of the decolorized polyethylene polyamine and water from the treatment mixture.

Polyethylene polyamines to which the present invention relates are compounds of the general formula:

$NH_2(CH_2CH_2NH)_nH$ wherein n is an integer from 1 to 5. Suitable polyethylene polyamines are predominately linear chain compounds having from 4 to 12 carbon atoms such as diethylenetriamine, triethylenetetramine, tetraethylenepentamine, pentaethylenehexamine and the like.

The discolored polyamines to which the present invention relates can be prepared by any of the processes well known in the art such as where a crude mixture of polyamines is produced and then subjected to refining procedures where desired individual polyamines or mixtures thereof are separated and recovered. The polyamine products recovered from the various refining or separation processes are, in general, discolored, having Gardner Color Nos. from about 1 to 14 or even higher.

The polyethylene polyamine hydrochlorides which may be used as a decolorizing agent in accordance with the present invention are prepared by reacting a polyethylene polyamine and hydrochloric acid. Suitable polyethylene polyamine hydrochlorides may be prepared in situ by adding hydrochloric acid, usually as an aqueous solution to the discolored polyethylene polyamine and then allowing a suitable time for reaction during which the solution is stirred. Also suitable for use is the polyethylene polyamine hydrochloride residue obtained from a prior decolorizing treatment of polyethylene polyamines which hydrochloride-containing residue is effective when suitable amounts of water are also present in the treating mixture.

The amount of polyethylene polyamine hydrochloride that should be employed is not narrowly critical and only a small amount may be needed. Usually the amount of polyethylene polyamine hydrochloride used is from 0.1 to 10 percent, and preferably 0.5 to 5, percent by weight of the HCI component based on the weight of polyethylene polyamine to be decolorized.

It is very important that water is present during the decolorizing treatment step (digestion step) to obtain the desired decolorization, though the amount of water required to be present is not narrowly critical. In general, from about 1 to about 12 percent by weight of water based on the weight of the decolorizing treatment mixture, and preferably from about 2 to 5 times the calculated weight of contained HCl, would be suitable though greater amounts of water may be present. The water may be added to the treatment mixture by itself, as a component of a hydrochloric acid solution, in combination with the polyamine hydrochloride residue, or in any other convenient manner.

After hydrochloric acid or polyethylene polyamine hydrochloride and water are added to the discolored polyethylene polyamines in a reaction vessel (digestion tank) the mixture is agitated and heated to a temperature within the range from about 200° C. to about 230° C. The mixture is maintained at a temperature within the range of at least about 180° C. up to a temperature at which the polyethylene polyamines will be discolored or decomposed (generally to about 240° C.), and preferably from about 200° C. to about 230° C. at pressures from around atmospheric to 100 psig, for the time necessary to obtain polyamines having the desired color values, generally from less than about 1 hour to about four hours. While the pressure that should be maintained in the digestion tank is not narrowly critical, it is preferred that the pressure used is high enough to maintain a substantial amount of the water in a liquid state, and pressures in the range from about 25 to 60 psig have been advantageously employed.

After completion of the decolorization reaction (digestion step), the decolorized polyethylene polyamines treatment mixture is subjected to a flash evaporation procedure by heating the mixture to a temperature in the range from about 170° C. up to 200° C. at reduced pressures, generally from about 25 mm Hg to 60 mm Hg absolute and the flash evaporated components are collected. Substantially colorless polyethylene polyamines and water are obtained as the flash evaporated products. The polyethylene polyamine hydrochlorides remain as a residue in the evaporator after completion of the flash evaporation step. It has been found that the temperature in the evaporator has a direct relation to the color of the refined polyamines and temperatures below 200° C. are especially preferred. The polyethylene polyamine hydrochloride containing residue which remains in the evaporator may be advantageously used for the decolorization treatment of further amounts of discolored polyamines as herein described or may be neutralized with an aqueous caustic solution to liberate the polyethylene polyamines which can be recovered by well known distillation procedures.

In an alternate procedure which may be run on a continuous basis, crude, discolored polyethylene polyamines are initially mixed with an aqueous solution of hydrochloric acid or with recycled polyethylene polyamine hydrochlorides in a circulated tank (digestion tank) maintained at a temperature in the range of from about 180° C. to about 240° C. and a pressure in the range of from atmospheric to 100 psig and preferably from about 25 psig to about 60 psig. Water is added to the mixture to maintain the amount thereof in the digestion tank at a level of about 2 to 5 times the calculated weight of hydrogen chloride contained in the polyamine hydrochlorides. During the continuous operation of the process, small amounts of an aqueous solution of hydrochloric acid are added to maintain the acid concentration in the digestion tank consistent with the desired color of the decolorized polyethylene polyamines and to replace acid which is periodically purged from the flash evaporator. The average residence time in the digestion tank may be from less than about 1 hour to about 4 hours depending on the color of the crude discolored polyethylene polyamine and amount of acid in the tank.

After an initial start up period in the digestion tank during which the initial charge of discolored polyamines have been treated for the desired length of time, portions of the treatment mixture can be fed continuously to a flash evaporator while additional amounts of discolored polyamines can be fed to the digestion tank. Refined, decolorized polyethylene polyamines are produced by flash evaporation in the evaporator at reduced pressures of less than 100 mm Hg absolute and preferably less than about 60 mm Hg absolute. The flash evaporator is maintained at a temperature up to 200° C., and preferably not exceeding about 180° C. In general, approximately 80-85 percent of the mixture fed to the evaporator is flash evaporated consisting of the refined polyethylene polyamines and substantially all of the water in the mixture. The water which is evaporated is separated from the refined polyethylene polyamines prior to condensation of the refined, decolorized polyamines.

The residue in the evaporator which comprises primarily polyethylene polyamine hydrochlorides is continuously recycled to the digestion tank and used to provide the hydrochloride decolorization agent for the treatment of further amounts of discolored, crude polyamines. Small amounts of the recycle polyamine hydrochloride residue from the evaporator may be periodically purged to prevent an excessive accumulation therein of heavy polyamines and to maintain a consistently low temperature in the flash evaporator since the temperature in the flash evaporator has a direct relation to the color of the refined polyamine products. The purged polyamine hydrochloride is generally neutralized and the heavier polyamines are recovered by distillation.

The invention will become more clear when considered with the following examples which are set forth as being merely illustrative of the invention and which are not intended in any manner, to be limitative thereof. Unless otherwise indicated, all parts and percentages are by weight.

Further, comparison of the hue of the decolorized polyamine products was carried out with reference to a platinum-cobalt (Pt—Co) hue standard. The Pt—Co hue standard was measured in accordance with ASTMD-1209-54. The hue standard is prepared in such a manner that 1.23 grams $K_2PtCl_6$ and 1,000 grams of $CoCl_1.6H_2O$ are dissolved in water and 100 ml. of hydrochloric acid having a specific gravity of 1.18 is added to the above solution and the resulting solution is diluted with water to obtain one liter and the resulting diluted solution is defined as hue standard no. 500. Further, by diluting it to 1/10 or 1/100, the hue standard No. 50 or No. 5 is obtained.

EXAMPLE 1

A charge of 1152 grams of crude triethylenetetramine (TETA) which contains small amounts of other heavy polyamines having a Gardner Scale Number of 12-13 is fed to a laboratory stirred kettle fitted with a short distillation column packed with stainless steel sponge, a goose-neck head, and a condenser, and 91 grams of a 37 percent aqueous solution of hydrochloric acid is added with stirring. The mixture is heated with stirring at 200° C. for 2.5 hours while sufficient water is refluxed to maintain the temperature at about 200° C. The pressure on the kettle is then reduced to 50 mm Hg absolute and at a temperature of 186° C., 800 grams of refined triethylenetetramine is flash evaporated from the kettle and condensed. The distillate has a color hue of 30 platinum-cobalt. A 25 gram sample of the residue in the kettle is removed and analysis shows it to contain 8.77 percent HCl.

An additional charge of 1152 grams of crude triethylenetetramine having a Gardner Number of 12-13 is fed to the kettle which contains the residue from the previous run of this example along with 47 grams of water and 36 grams of a 37 percent aqueous solution of hydrochloric acid. The mixture is heated at 200° C. with stirring for 2.5 hours and then allowed to stand for an additional 16 hours at 200° C. The pressure on the kettle is then reduced to 50 mm Hg absolute and the mixture is subjected to flash evaporation at 186° C. 956 grams of refined triethylenetetramine is flash evaporated and then condensed. The refined TETA is determined to have a color hue of 15 Pt—Co. A 25 gram sample of the residue in the tank is removed and determined to contain 8.99 percent of HCl.

A third portion of 1152 grams of the same crude TETA as used in the first two runs of this example is charged along with 100 grams of water to the kettle which contains the residue from the previous two runs of this example. The mixture is heated at 200° C. with stirring for four hours after which the pressure is reduced in the kettle to 50 mm Hg absolute. At a flash evaporation temperature of 196° C., 950 grams of refined TETA is evaporated and then condensed. The refined TETA is determined to have a color hue of 25 Pt—Co.

EXAMPLE 2

Using the apparatus of Example 1, 746 grams of crude triethylenetetramine (TETA) having a Gardner Scale color of 14 which contains small amounts of other polyamines is mixed with 58 grams of 37 percent hydrochloric acid with stirring. The mixture is heated at 200° C. with stirring for 1.5 hours. The pressure in the reactor is then reduced to 50 mm Hg absolute and at temperatures in the range of 195° C. to 205° C., 652 grams of TETA is evaporated and then condensed. The color hue of the refined TETA is determined to be 70 Pt—Co but it is noted that during evaporation of the TETA, the color of the last portion evaporated at 205° F. increased significantly. A sample of 33 grams of the residue remaining after the evaporation step is removed from the tank. A series of 7 additional runs are made by adding additional charges of crude TETA to the residue in the reactor along with make-up amounts of hydrochloric acid and water. The proportion of ingredients employed in each of the runs of this example, and the color of refined TETA obtained from each run is summarized in Table 1. Each of the charges of crude TETA employed have a Gardner Scale color of 14.

TABLE I

| Run No. | TETA Crude gms added | Makeup[c] HCl, gms | Makeup $H_2O$, gms | Final Evap. temp. °C. | Final Pressure mm Hg, Abs. | Residue Purge, gms | Refined TETA gms - Pt-Co. Color |
|---|---|---|---|---|---|---|---|
| 1 | 746 | 58.0 | — | 205 | 50 | 33 | 652 70 |
| 2 | 612 | 11.0 | 36 | 195 | 25 | 33 | 541 65 |
| 3 | 610 | 8.25 | 36 | 191 | 20 | 33 | 562 60 |
| 4 | 612 | 5.50 | 36 | 190 | 25 | 33 | 563 60 |
| 5 | 612 | 2.75 | 36 | 190 | 25 | 33[a] | 569 60 |
| 6 | 612 | — | 36 | 190 | 25 | 33 | 544 65 |
| 7 | 612 | — | 36 | 190 | 25 | 33 | 557 60 |
| 8 | 612 | — | 36 | 190 | 25 | 263[b] | 555 55 |

[a]Assayed 8.19% HCl
[b]Final residue
[c]37% Concentration in water

EXAMPLE 3

A mixture containing 500 grams of crude tetraethylenepentamine (TEPA) and 40 grams of 37 percent hydrochloric acid is charged to a stirred autoclave with 10 grams of water. The autoclave is closed and the contents thereof are heated with agitation to 215° C. under autogenous (about 50 psig) pressure for two hours. The contents of the autoclave are then charged to a single-stage distillation apparatus where 75 percent of the organic materials are evaporated over a temperature range of 140° C. to 168° C. at 1 mm Hg absolute pressure.

The distillate is determined to contain 88 percent of tetraethylenepentamine having a color hue of 100 Pt—Co. The organic residue in the evaporator (distillation apparatus) is determined to contain 15 percent HCl.

EXAMPLE 4

A stirred 500 ml kettle with a short column section packed with stainless steel sponge, a goose-neck head, and condenser are employed in this Example to carry out a series of runs. While each of the runs of this example are performed in a batch operation, they are carried out in a cyclic manner to simulate a continuous system with a procedure including recycle and purge of evaporator residues from previous runs being used. A charge of 200 grams of crude, discolored polyamines containing about 95% triethylenetetramine, small amounts of other polyamines and about 0.25 weight percent of HCl is used in each run. The digestion temperature is held at 200° C. for 3 hours except where noted otherwise in each of the runs of the example. The operating conditions, proportion of ingredients used, and color properties for products produced for each of the runs are summarized in Table II.

The results reported in Table II show that the increasingly higher flash evaporation temperatures employed in Run Nos. 1–4 result in progressively higher product color, Run No. 5 shows that the use of a lower digestion temperature results in higher color, Run Nos. 9–12 show that the color of refined TETA becomes progressively higher when HCl is not added to make-up for HCl removed from the system by purging the evaporator residue.

TABLE II

| | | | | | | | |
|---|---|---|---|---|---|---|---|
| | | | CONDITIONS AND RESULTS OF CYCLIC TESTS | | | | |
| Run No | TETA Charge (grams) | Makeup HCl (grams) | Makeup H$_2$O (grams) | Refined TETA (grams) | Residue Purge (grams) | Residues, Wt. % HCl | Final Flash Temp., °C. | TETA Color Pt-Co |
| 1 | 200 | 5.5 | 13 | 165 | 5 | 14.2 | 183 | 26 |
| 2 | 200 | 0.0 | 13 | 199 | 5 | 15.4 | 195 | 38 |
| 3 | 200 | 0.0 | 13 | 196 | 0.0 | 16.7 | 214 | 61 |
| 4 | 200 | 0.0 | 13 | 196 | 5 | 16.7 | 223 | 105 |
| 5[a] | 200 | 0.0 | 13 | 196 | 0.0 | — | 225 | 200 |
| 6 | 200 | 0.0 | 13 | 175 | 5 | 10.0 | 193 | 75 |
| 7 | 200 | 0.0 | 13 | 184 | 5 | 9.4 | 189 | 54 |
| 8 | 200 | 1.6 | 13 | 183 | 5 | 11.2 | 200 | 54 |
| 9 | 200 | 0.0 | 13 | 195 | 5 | 11.7 | 204 | 83 |
| 10 | 200 | 0.0 | 13 | 195 | 5 | 10.9 | 204 | 80 |
| 11 | 200 | 0.0 | 13 | 195 | 5 | — | 215 | 87 |
| 12 | 200 | 0.0 | 13 | 195 | 5 | 10.1 | 231 | 176 |
| 13[b] | 200 | 0.0 | 13 | 195 | 10 | 9.6 | 230 | 170 |
| 14 | 200 | 0.5 | 13 | 190 | 10 | 11.1 | 239 | 200 |
| 15[c] | 200 | 0.5 | 13 | 165 | 10 | 7.3 | 195 | 102 |
| 16 | 200 | 1.5 | 13.5 | 189 | 10 | 9.9 | 195 | 73 |
| 17 | 200 | 1.5 | 13.5 | 179 | 10 | 10.1 | 195 | 71 |
| 18 | 200 | 1.0 | 13 | 179 | 10 | 10.8 | 198 | 106 |
| 19 | 200 | 1.0 | 13 | 179 | 10 | 11.1 | 198 | 95 |
| 20 | 200 | 1.0 | 13 | 184 | 10 | 11.6 | 196 | 101 |

[a] For Cycle 5 only, the goose-neck head was replaced with a total condenser to prevent water from leaving the system. This resulted in a digestion temperature of 177° C.
[b] Residue purge rate was increased.
[c] Flash was held to 195–198° C. (maximum) temperature.

What is claimed is:

1. A process for producing decolored polyethylene polyamines having the general formula NH$_2$(CH$_2$CH$_2$NH)$_n$H wherein n is an integer of 1 to 5 from discolored polyethylene polyamines which comprises treating the discolored polyethylene polyamines with polyethylene polyamine hydrochloride in the presence of water at elevated temperatures for the time necessary to reduce the color of said polyethylene polyamine and then flash evaporating the decolored polyethylene polyamine from the treating mixture.

2. The process of claim 1 wherein the treatment step for discolored polyamines is carried out at pressures high enough to maintain water in the liquid phase.

3. The process of claim 1 wherein the treatment step is carried out at temperatures with range of at least 180° C. to about 240° C.

4. The process of claim 1 wherein the flash evaporation step is carried out at reduced pressures at temperatures in the range of from about 170° C. to 200° C.

5. The process of claim 1 wherein the polyethylene polyamine hydrochloride is formed in situ by adding hydrochloric acid and water to the polyethylene polyamines prior to the treatment step.

6. The process of claim 1 wherein the polyethylene polyamine comprises a linear chain polyethylene polyamine having from 4 to 12 carbon atoms.

7. The process of claim 1 wherein the treatment step is carried out at temperatures in the range of about 200° C. to about 230° C. at pressures in the range from about atmospheric pressure to about 100 psig.

8. The process of claim 1 wherein the amount of polyethylene polyamine hydrochloride used in the treatment step is from 0.1 to 10 percent by weight of the HCl component based on the weight of polyethylene polyamine to be decolorized.

9. The process of claim 1 wherein the polyethylene polyamine hydrochloride is the evaporator residue from the hydrogen chloride decolorization treatment of polyethylene polyamines.

10. A process for continuously producing polyethylene polyamines with improved color properties having the general formula:

NH$_2$(CH$_2$CH$_2$NH)$_n$H wherein n is an integer of 1 to 5 from discolored polyethylene polyamines which comprises treating discolored polyethylene polyamines with polyethylene polyamine hydrochloride in the presence of water at elevated temperatures for the time necessary to reduce the color of said discolored polyethylene polyamines, flash evaporating the decolorized polyethylene polyamine from said polyethylene polyamine hydrochloride-containing treatment mixture, and then employing the polyethylene polyamine hydrochloride-containing residue from the flash evaporation step for use in treating further amounts of discolored polyethylene polyamines in the presence of water at elevated temperatures.

11. The process of claim 10 wherein treatment steps are carried out at pressures high enough to keep water in the liquid state.

12. The process of claim 10 wherein the treatment steps are carried out at pressures in the range of from atmospheric pressure to about 100 psig.

13. The process of claim 10 wherein the treatment steps are carried out at temperatures in the range of from about 180° C. to about 240° C.

14. The process of claim 12 wherein the treatment steps are carried out at temperatures in the range of from about 180° C. to about 240° C.

15. The process of claim 10 wherein the flash evaporation step is carried out at reduced pressures at a temperature in the range of from about 170° C. to 200° C.

16. The process of claim 10 wherein the amount of polyethylene polyamine hydrochloride used in the treatment steps is from 0.1 to 10 percent by weight of the HCl component based on the weight of polyethylene polyamines to be decolorized.

17. The process of claim 10 wherein the residence time of the discolored polyethylene polyamines treatment mixture in the treatment step is at least about one hour.

18. A process for producing decolored polyethylene polyamines having the general formula NH$_2$(CH$_2$CH$_2$NH)$_n$H wherein n is an integer of 1 to 5 from discolored polyethylene which comprises treating the discolored polyethylene polyamines with polyethylene polyamine hydrochloride in the presence of water at elevated temperatures between at least about 180° C. and about 240° C. for the time necessary to reduce the color of said polyethylene polyamine and then flash evaporating the decolorized polyethylene polyamine from the treating mixture at reduced pressure and in the temperature range of from about 170° C. up to 200° C.

19. A process for continuously producing polyethylene polyamines with improved color properties having the general formula:

NH$_2$(CH$_2$CH$_2$NH)$_n$H wherein n is an integer of 1 to 5 from discolored polyethylene polyamines which comprises treating discolored polyethylene polyamines with polyethylene polyamine hydrochloride in the presence of water at elevated temperatures between at least about 180° C. and about 240° C. for the time necessary to reduce the color of said discolored polyethylene polyamines, flash evaporating the decolorized polyethylene polyamine from said polyethylene polyamine hydrochloride-containing treatment mixture at reduced pressures and in the temperature range of from about 170° C. to about 200° C., and then employing the polyethylene polyamine hydrochloride-containing residue from the flash evaporation step for use in treating further amounts of discolored polyethylene polyamines in the presence of water at elevated temperatures.

* * * * *